(12) United States Patent
Schulz et al.

(10) Patent No.: US 6,534,754 B2
(45) Date of Patent: *Mar. 18, 2003

(54) MICROWAVE OFF-GAS TREATMENT APPARATUS AND PROCESS

(75) Inventors: Rebecca L. Schulz, Aiken, SC (US); David E. Clark, Gainesville, FL (US); George G. Wicks, North Aiken, SC (US)

(73) Assignee: Westinghouse Savannah River Company, L.L.C., Aiken, SC (US)

(*) Notice: Subject to any disclaimer, the term of this patent is extended or adjusted under 35 U.S.C. 154(b) by 63 days.

This patent is subject to a terminal disclaimer.

(21) Appl. No.: 09/734,504

(22) Filed: Dec. 11, 2000

(65) Prior Publication Data

US 2001/0003338 A1 Jun. 14, 2001

Related U.S. Application Data

(63) Continuation-in-part of application No. 09/382,758, filed on Aug. 25, 1999, which is a continuation-in-part of application No. 08/911,411, filed on Aug. 14, 1997, now Pat. No. 5,968,400.

(51) Int. Cl.[7] .................................................. H05B 6/80
(52) U.S. Cl. ........................................ 219/679; 219/686
(58) Field of Search ................................ 219/679, 686, 219/680, 681, 682, 678, 701, 730, 756–757, 759; 422/21

(56) References Cited

U.S. PATENT DOCUMENTS

| 5,035,858 | A |   | 7/1991  | Held et al. |
|-----------|---|---|---------|-------------|
| 5,213,758 | A |   | 5/1993  | Kawashima et al. |
| 5,270,000 | A |   | 12/1993 | Goldner et al. |
| 5,270,515 | A |   | 12/1993 | Long |
| 5,277,868 | A |   | 1/1994  | Langford |
| 5,322,603 | A |   | 6/1994  | Kameda et al. |
| 5,348,235 | A |   | 9/1994  | Pappas |
| 5,429,799 | A |   | 7/1995  | Sheih et al. |
| 5,441,622 | A |   | 8/1995  | Langford |
| 5,507,927 | A |   | 4/1996  | Emery |
| 5,540,886 | A |   | 7/1996  | Warmbier et al. |
| 5,830,328 | A |   | 11/1998 | Uhm |
| 5,835,866 | A | * | 11/1998 | Bridges et al. ................ 588/19 |
| 5,858,303 | A |   | 1/1999  | Schiffmann et al. |
| 5,968,400 | A |   | 10/1999 | Wicks et al. |
| 6,159,422 | A | * | 12/2000 | Graves et al. ................ 422/22 |

* cited by examiner

Primary Examiner—Teresa Walberg
Assistant Examiner—Quang Van
(74) Attorney, Agent, or Firm—Dority & Manning, PA

(57) ABSTRACT

The invention discloses a microwave off-gas system in which microwave energy is used to treat gaseous waste. A treatment chamber is used to remediate off-gases from an emission source by passing the off-gases through a susceptor matrix, the matrix being exposed to microwave radiation. The microwave radiation and elevated temperatures within the combustion chamber provide for significant reductions in the qualitative and quantitative emissions of the gas waste stream.

7 Claims, 2 Drawing Sheets

MICROWAVE OFF-GAS TREATMENT APPARATUS AND PROCESS

RELATED APPLICATIONS

This application is a Continuation-in-Part of application Ser. No. 09/382,758 filed Aug. 25, 1999, entitled "Medical Waste Treatment and Decontamination System" which is incorporated herein by reference, and which is a Continuation-in-Part to application Ser. No. 08/911,411 filed Aug. 14, 1997, now U.S. Pat. No. 5,968,400 entitled "Tandem Microwave Waste Remediation and Decontamination System" which is also incorporated herein by reference,

STATEMENT AS TO RIGHTS TO INVENTIONS MADE UNDER FEDERALLY SPONSORED RESEARCH AND DEVELOPMENT

The U.S. Government has rights in this invention pursuant to Contract No. DE-AC09-89SR18035 and Contract No. DE-AC09-96SR18500 between Westinghouse Savannah River Company and the U.S. Department of Energy.

BACKGROUND OF THE INVENTION

1. Field of the Invention

This invention relates to the use of microwave energy to treat multi-component gaseous waste streams. Gaseous waste streams, referred to generally herein as "off-gas", are ubiquitous in all areas of industry and manufacturing. A multitude of industrial processes generates waste off-gas streams which may include a variety of undesirable contaminants, such as volatile organic compounds (VOCs). Thermal processing of solid and liquid waste will frequently generate a separate gaseous waste stream which should desirably be treated prior to release into the environment. At present, gaseous waste streams are frequently treated with filtration systems, chemical cleansing, scrubbers, or chemical conversion to a solid material which is subsequently disposed of as solid waste. However, such methods are expensive and require specialized materials and handling which adds to the disposal and treatment expense. Further, such off-gas treatment methods are not generally suitable or economically feasible for a small volume generator of a contaminated off-gas stream. Unfortunately, small businesses that use or manufacture solvent based VOC materials, such as a dry cleaners, a painting shop, etc., may simply exhaust or discharge the materials into the environment.

Accordingly, there is a need for a low cost, simple to operate waste treatment apparatus and process for low volume gaseous waste generators. Further, there remains a need for further improvement in existing VOC and other gas waste treatment systems over currently available technology. As a result, there remains much room for improvement and variation within the art.

2. Description of Related Art

It is known in the art to use microwaves to treat solid waste. U.S. Pat. No. 5,166,488 to Peppard, incorporated herein by reference, teaches an apparatus which uses microwaves to melt hypodermic syringes. U.S. Pat. No. 4,940,865 provides an apparatus for melting materials using microwaves. However, these microwave treatments result in the generation of gaseous and airborne particulates which require costly filtering and containment systems.

U.S. Pat. No. 5,507,927 to Emery discusses an apparatus for the reduction of organic material through the use of microwave radiation. However, the process taught by Emery results in gaseous products being evolved which are taken to a condenser and condensed to a liquid product.

U.S. Pat. No. 5,270,515 to Long is directed to a microwave plasma process for detoxification of dioxins, furans, and other toxicants. This reference teaches using microwaves to create an ionized plasma state which is controlled through an induced magnetic field. The plasma is used to produce high ionization levels and molecular dissociation without excess heating of the reactants. Such an apparatus and process requires considerable infrastructure and control mechanisms.

U.S. Pat. No. 5,830,328 to Uhm is also directed to using microwave radiation to generate a plasma to decontaminate gaseous emissions. The microwave radiation is conducted through an electric field for generation of a plasma having a high electron temperature. Material is exposed to the plasma for oxidation of the contaminants by atomic oxygen. Uhm requires the specialized equipment and control mechanisms for the creation of a plasma field, and requires the use of plasma torches and other apparatuses so as to maintain a temperature in excess of 3,000 K.

The use of plasma ion fields requires a high investment and operator sophistication which is not economically feasible for many users. Accordingly, there remains room for improvement within the art of microwave processing of gaseous waste.

SUMMARY OF THE INVENTION

It is an object of this invention to provide an apparatus and a process to treat off-gas emissions with microwave radiation such that the treated off gas may be discharged into the atmosphere.

It is a further and more particular object of this invention to provide a microwave treatment apparatus useful in the treatment of off-gases.

It is a further and more particular object of this invention to provide an off-gas disposal apparatus and process which uses hybrid microwave heating to treat a wide range of materials contained in off-gas streams.

It is still a further and more particular object of this invention to provide an apparatus and process which can be used to regenerate or purify a stream of an inert process gas in a gas recycling or recovery system.

It is a further object of the present invention to allow for the sterilization of a gaseous stream.

It is an additional object of the present invention to provide an off-gas treatment process in which microwave energy is used to purify an air stream and in which latent heat associated with the purification process is recovered.

It is a further object of the present invention to provide an air purification process and apparatus which can be used to reduce the concentration of odor-causing compounds present in the off-gas system.

It is still a further object of the present invention to provide a microwave purification process and apparatus which allows replacement of catalytic converters from waste streams associated with the combustion of hydrocarbons.

It is still a further object of the invention to develop a small, compact, portable off-gas system of low maintenance, that can be interfaced with various furnaces, ovens or other thermal equipment generating off-gases and to remediate the gases produced during operation.

These and other objects of the invention are accomplished by an apparatus and process that provides for a hybrid microwave off-gas treatment system comprising:

a treatment chamber in communication with a source of microwaves, the treatment chamber having an inlet in communication with an off-gas source, a treatment chamber further defining a susceptor defining a gas permeable matrix in communication with the input region; and an exhaust outlet in communication with an output region of the treatment chamber, wherein off-gases pass through the inlet into the susceptor region of the treatment chamber whereby the susceptor matrix is maintained at an effective temperature for treating the off-gases, the treated off-gases exiting through an exhaust port.

Such an apparatus enables the process of treating off-gases comprising:

providing a fluid stream having at least one contaminant therein;

directing the fluid stream to a treatment chamber;

radiating the fluid stream in the treatment chamber with microwave energy;

retaining the fluid stream within the treatment chamber until an effective amount of the at least one contaminant is destroyed, thereby providing a treated fluid stream; and venting the treated fluid stream.

The invention is an improvement over prior methods of using microwave energy to treat gaseous waste. The present invention provides an off-gas treatment process such that a releasable off-gas is produced. Contaminants within the off-gases are combusted to innocuous end products and/or releasable concentrations. The microwave process provides a high temperature environment produced by microwave energy in combination with a susceptor material. The resulting treated off-gas waste is a decontaminated and sterilized off-gas system in which key emissions can be significantly reduced and often may be vented into the atmosphere.

DETAILED DESCRIPTION OF THE INVENTION

Figure 1:
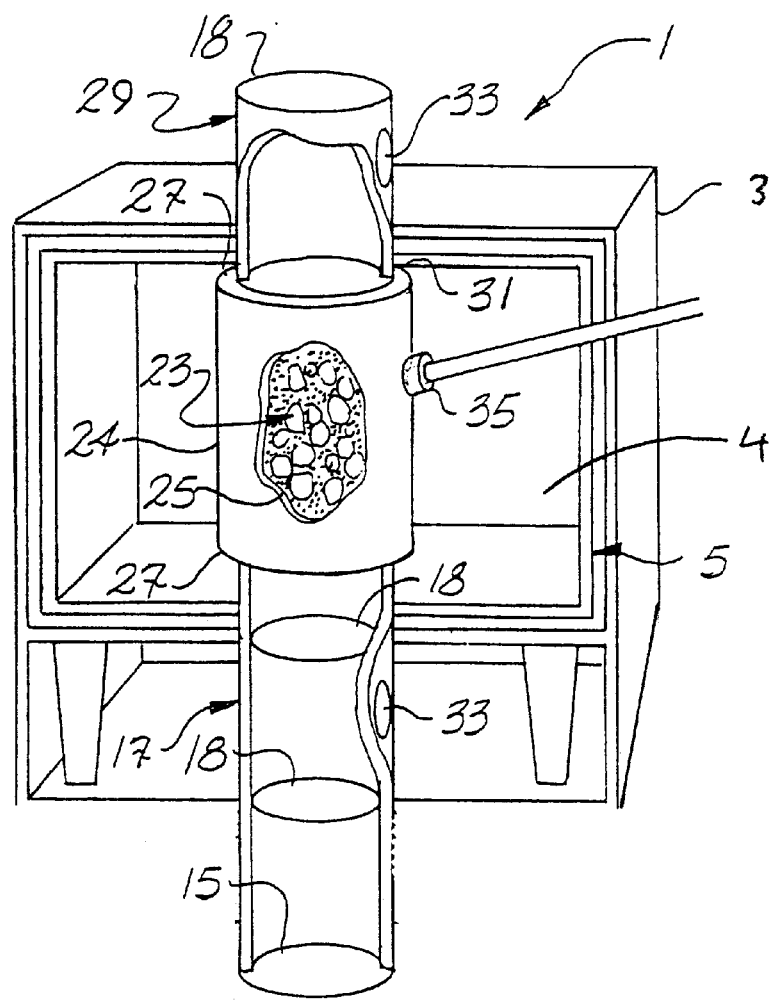
FIG. 1 depicts a schematic of a microwave off-gas treatment apparatus in accordance with this invention.
Figure 1:
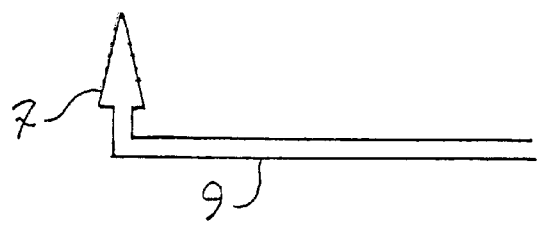

As seen in reference to FIG. 1, one embodiment of a microwave off-gas treatment apparatus 1 is illustrated. Off-gas treatment apparatus 1 uses a commercially available microwave unit 3 having the conventional time and power level controls (not illustrated). A variety of commercially available microwave units are available. By way of example, a conventional unit provides an output of 900 watts at 2.45 GHz as was used in the collection of data set forth below. Microwave unit 3 defines an interior chamber 4 which may have the interior chamber surfaces lined with a refractory lining 5.

A conduit, seen in the figures as a hollow tube 17, is in communication through a lower surface of the microwave unit with the interior chamber 4. A segment of tube 17 further defines a treatment chamber 23. Treatment chamber 23, seen here in the form of a tube 24, may be constructed of a refractory material (St. Gobain/Norton Industrial Ceramic Corporation). Tube 24 defines an interior volume partially filled with a bed of susceptor materials such as SiC 16 grit.

Alternatively, chamber 23 can be filled with a plurality of stacked, reticulated SiC filters as well as other appropriate susceptor materials (such as refractory materials used to make fire bricks) and mixtures thereof. Chamber 23 and susceptor material 25 provide operating temperatures within the treatment chamber of between 1,000 to 1,200° C. Reticulated phosphate bonded alumina (PBA) filters 27 may be placed at either end of chamber 23 to maintain the stability of the bed and to increase the gas emission residence time in the chamber. Design features for the treatment chamber, such as a serpentine pathway or non-linear tube, can also be used to increase residence time. Further, the passageway which defines chamber 23 may be of any shape or configuration which permits the passage of the off-gas. Optional filters 18 may be provided along the interior of tube 17, the filter type varying depending upon the physical and chemical characteristics of constituents within the off-gas stream.

Tube 17 defines an intake end 15 and outlet end 29. In the illustrated embodiment, intake 15 is positioned beneath the microwave unit 3, and the outlet 29 is in communication through an upper surface of unit 3. However, any configuration or placement of the intake 15 or outlet 29 which operatively provides for an entry of off-gas into the microwave unit and an outlet for the discharge of the treated off-gas may be used and is envisioned in accordance with the present invention.

Off-gas stream 7 may be supplied via a separate remote supply line 9 or may be introduced directly from an off-gas source such as an integrated solid waste treatment apparatus as set forth in applicants' related applications referenced above. The off-gas treatment process is easily adapted for a wide variety of gaseous waste streams and is highly effective in treating diverse mixtures of VOCs within a single waste stream.

It may be desirable to use an inert gas, such as nitrogen, to reduce the volatility of an off-gas stream prior to introducing the off-gas stream into the treatment apparatus. In addition, the size, scale, and design parameters of the treatment apparatus may be varied to accommodate the volume, flow rate, and other characteristics of the off-gas. In the simplest embodiment, a commercially available microwave oven can be adapted to have the treatment chamber operatively disposed within the interior chamber 4.

Sampling ports 33 may be provided on outlet port 29 as well as intake 15 (not pictured) to facilitate collection of gas stream samples for analysis. A thermocouple 35 may be provided on treatment chamber 23 to provide displayed operating temperature conditions.

In operation, microwave unit 3 is operated to bring the SiC susceptor material 25 within chamber 23 to an operating temperature of between about 1,000–1,200° C. Once the operating temperature conditions are obtained, an off-gas stream 7 is introduced into intake 15.

Figure 2:
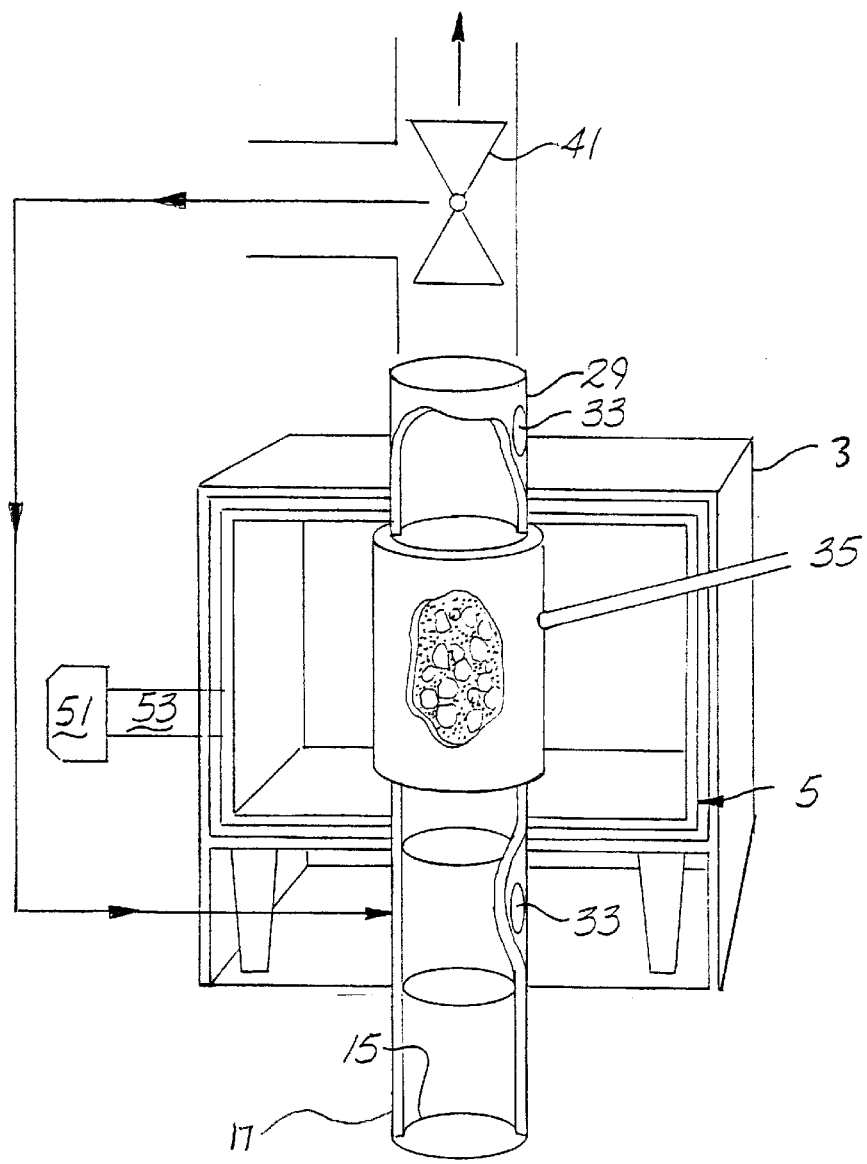
FIG. 2 depicts an alternative schematic configuration of the microwave off-gas treatment apparatus of this invention.
Figure 2:

The process can be further controlled by the use of inert gases to provide a regulated fluid flow through the system. The sampling ports 33 provide the operator the ability to sample incoming and treated off-gas streams. The data from the following examples were collected by using Tenax-TA filled glass air traps (OI Analytical, College Station, Tex.) which are highly absorbent for C6–C20 compounds. Following collection, the air traps can be submitted for gas chromatography and mass spectrometry (GC-MS) analysis of the retained off-gases. It is envisioned that sampling ports 33 may be equipped with in-line monitors to provide real-time data collection with respect to off-gas constituents. As seen in FIG. 2, a valve 41 can be used to control the venting of treated off-gases. Should on-line monitors detect unacceptable levels of materials in the off-gas stream, the off-gas pathway can be diverted for retreatment (see directional arrows) to the off-gas treatment chamber. If desired, the treated off-gas may be directed to a second treatment chamber for additional processing.

As set forth in applicants' related application having Ser. No. 09/911,411, now U.S. Pat. No. 5,968,400, a tandem microwave system has demonstrated its effectiveness in treating numerous gaseous organic chemicals, rendering the treated off-gas to non-detectable concentrations and/or reductions of one order of magnitude. The following examples are indicative of a diverse organic gas waste stream for demonstrating the efficacy of the microwave off-gas treatment process. While the examples set forth below use circuit boards as a source of organic materials, a variety of hazardous compounds as seen in Table 2 are generated from the thermal destruction of the circuit boards. It is this diverse gas which is subsequently treated by the microwave off-gas apparatus as set forth below.

However, it is understood that a multitude of hazardous gas waste streams could be used as the source material for the off-gas treatment process described herein.

certain organic chemical off-gas concentrations to non-detectable (ND) concentrations, and reductions of other organic chemical off-gas concentrations to more than 1 order of magnitude.

TABLE 1

| Sample ID | Initial Weight (g) | Final Weight | % Wt Loss | Processing/Off-gas Collection Time (mm) | Duty Cycle* (%) |
|---|---|---|---|---|---|
| SR1 | 69.96 | 41.15 | 41.2 | 30 | 50 |
| SR2 | 70.09 | 40.66 | 41.9 | 30 | 50 |
| SR3 | 69.99 | 45.75 | 34.6 | 30 | 50 |
| SR4 | 70.05 | 41.16 | 41.2 | 30 | 100 |
| SR5 | 70.01 | 42.27 | 39.6 | 30 | 50 |
| SR6 | 70.00 | 40.85 | 41.6 | 30 | 50 |
| SR7 | 70.03 | 44.49 | 36.4 | 30 | 50 |

*Percent of time interval magnetron was activated

TABLE 2

A Summary of the GC mass Spectroscopy Results of Off-Gas Emissions Resulting from Combustion of Printed Circuit Boards.
(A = before microwave off-gas treatment; B = after microwave off-gas treatment).

| Compound | SR-1 (ppb) A | B | SR-2 (ppb) A | B | SR-3 (ppb) A | B | SR-4 (ppb) A | B | SR-5 (ppb) A | B | SR-6 (ppb) A | B | SR-7 (ppb) A | B |
|---|---|---|---|---|---|---|---|---|---|---|---|---|---|---|
| Benzene* | 16.9 | 1.1 | 14.2 | nd | 19.8 | nd | 115.3 | 5.2 | 119.6 | 8.1 | 176.6 | 14.7 | 165.4 | 13.5 |
| Toluene | 28.7 | 2.7 | 24.4 | nd | 32.6 | nd | 67.5 | 6.1 | 78.7 | 6.9 | 159.1 | 18.1 | 115.7 | 5.9 |
| Ethylbenzene* | 18.7 | nd** | 19.0 | nd | 7.8 | nd | 13.9 | nd | 26.7 | nd | 142.9 | 5.0 | 91.8 | nd |
| Styrene* | 38.7 | 1.2 | 66.6 | nd | 15.0 | nd | 165.2 | 2.9 | 167.7 | 2.6 | 472.3 | 27.2 | 482.9 | 6.5 |
| Napthalane* | 1.2 | nd | 11.0 | nd | nd | nd | 75.1 | 1.3 | 35.2 | 1.3 | 6.8 | 3.4 | 47.6 | 2.4 |
| m/p Xylene* | 17.5 | nd | 1.9 | nd | nd | nd | 27.5 | nd | 23.8 | nd | 53.3 | 1.6 | 60.0 | nd |
| 1,3,5 Trimethylbenzene | 9.5 | nd | 12.4 | nd | 1.3 | nd | 15.6 | 1.6 | 18.4 | nd | 12.8 | 2.4 | 46.2 | 1.7 |
| 1,2,4 Trimethylbenzene | 17.5 | nd | 1.7 | nd | nd | nd | nd | nd | nd | nd | 15.1 | nd | 6.1 | 1.8 |

*Listed in the Clean Air Act (as amended, 1990) as hazardous air pollutants [14].
**nd = not detected (<1 ppb)

EXAMPLE 1

Set forth in Tables 1 and 2 are the conditions and results of seven 30 minute test runs (SR-1 through SR-7) using crushed and pulverized printed electrical circuit boards as the waste material. Circuit board material was initially selected as a test material since circuit boards have a mixture of organics and metal. The material is also dense and the organic material will produce a high volume of diverse off-gases which will require treatment. The data was collected using a side-by-side microwave unit configuration as disclosed and discussed in Schulz, R. L., Folz, D. C., Clark, D. E., Schmidt, C. J. and Wicks, G. G., "Microwave Treatment of Emissions from Waste Materials", Microwave Processing of Materials V, M. F. Iskander, J. O. Kiggans, Jr., C. Bolomey, eds., Materials Research Society Symposium Proceedings, Vol. 430, pp. 549–554 (1996).

The gaseous organic compounds that vaporize during treatment of the material in the primary chamber, were sampled at a gas sampling port at the exit of the solids treatment chamber. These values are provided in column A in Table 2. The gases were sampled following treatment in the off-gas treatment chamber and the values reported in column B of Table 2. The results demonstrate reduction of

EXAMPLE 2

Set forth in Table 3 below is data from two additional runs using crushed and pulverized circuit boards and following the general protocol set forth above in an upper/lower tandem microwave system as seen in FIG. 1. As set forth in Table 3, the results of the emissions analysis is set forth in nanograms. Again, significant reductions and/or elimination of certain emission waste has been obtained.

TABLE 3

Gas Chromatography Data Collected Before and After Microwave Treatment of Emissions Resulting From the Treatment of Unreinforced Circuit Boards

| COMPOUND | SR-8 EMISSIONS (ng) A | B | SR-9 EMISSIONS (ng) A | B |
|---|---|---|---|---|
| Benzene* | 5838.9 | 22.2 | 1415.6 | 139.5 |
| Toluene* | 8146.6 | 15.7 | 4215.9 | 158.7 |
| Ethylbenzene* | 1147.4 | nd | 4557.0 | 5.2 |
| Styrene* | 1666.9 | 6.2 | 20012.0 | 38.4 |

TABLE 3-continued

Gas Chromatography Data Collected
Before and After Microwave Treatment of Emissions
Resulting From the Treatment of Unreinforced Circuit
Boards

| COMPOUND | SR-8 EMISSIONS (ng) | | SR-9 EMISSIONS (ng) | |
|---|---|---|---|---|
| | A | B | A | B |
| Naphthalene* | 355.5 | nd | 2403.6 | 27.9 |
| m/p Xylene* | 2259.0 | nd | 510.6 | nd |
| 1,3,5 Trimethylbenzene | 1564.0 | nd | 378.7 | 64.3 |
| 1,2,4 Trimethylbenzene | 904.7 | nd | 171.8 | nd |

A = before microwave off-gas treatment; B = after microwave off-gas treatment
*Listed in the Clean Air Act (as amended, 1990) as hazardous air pollutants.

The reductions in off-gas constituents are significant, in some cases three orders of magnitude, and have applications for a variety of off-gas emission sources, regardless of origin. Further, the data is from a treatment chamber having a simple cylindrical shape and a length of approximately 9 inches. By varying the geometry and length of the treatment chamber, it is possible to increase the volume of introduced off-gases, increase residence time and enhance the efficiency of the treatment process.

For instance, the use of a standard retail microwave unit requires little space, is compatible with existing electrical supply needs, and the operation of which is well known and easily learned.

In preferred embodiments of the present invention, it is desirable to have operating safeguards in place. One such safeguard is the use of a thermocouple or thermostat to monitor the temperature of the off-gas unit. The delivery of a treatment gas to the off-gas microwave unit can be designed to be inoperative until a sensor or switch is activated in response to an adequate decomposition temperature within the off-gas unit. When controlled in this manner, the generation of off-gases from the microwave treatment process does not occur until the off-gas treatment unit is operative.

The present invention makes use of both direct microwave energy bombardment of the waste material along with radiant infrared heating which occurs through the use of susceptor materials. It is also possible to tune or vary the frequency of the microwave source so as to selectively target certain types or categories of waste constituents. Such targeting is possible in both the primary waste step as well as in the treatment of off-gas emissions.

For instance, it is possible to use separate magnetrons at separate frequencies to sequentially treat off-gases with varying frequencies. For large capacity industrial uses, it is preferred that microwaves be generated from one or more remote magnetrons 51 (FIG. 2) and transmitted via waveguides 53. This arrangement shields the magnetron from reflecting microwaves. It also permits innovative designs for treatment chambers to be constructed and may be useful in the design of large volume commercial units. The location of a remote magnetron is particularly useful in developing customized designs for controlling off-gas emissions.

As set forth in the data above, the present invention provides a process which significantly reduces the emission levels of treated gas.

The present invention has useful applications for small scale waste generators such as research laboratories as well as smaller-scale business operations. As stated earlier, conventional microwave units are compatible with a simple embodiment of the present invention. It is advisable to provide a door locking mechanism responsive to the internal temperature of the susceptor and/or treatment container so as to prevent the opening of the microwave unit until an adequate cool-down period has elapsed. This feature protects the operator from potentially serious burns as well as preventing a sudden influx of air into a partially combusted heated off-gas sample. The sudden influx of air could result in an unwanted flashing of the treated off-gas waste.

While one or more preferred embodiments of the invention have been described above, it should be understood that any and all equivalent realizations of the present invention are included within the scope and spirit thereof. For example, the present invention may be embodied with a variety of different microwave units. It should be understood by those of ordinary skill in this art that the present invention is not limited to these embodiments, since modifications can be made. Further, such variations from the preferred embodiment would be expected in large scale applications capable of handling large volume generators of a gas waste stream. Therefore, it is contemplated that any and all such embodiments are included in the present invention as may fall within the literal or equivalent scope of the following appended claims.

What is claimed is:

1. An off-gas treatment apparatus comprising:
   a treatment chamber for the destruction/decomposition of a gas stream having an inlet, an outlet, and a matrix core between the inlet and the outlet, the matrix core further comprising a gas permeable susceptor said inlet adapted for receiving a pressurized gas stream comprising gaseous organic contaminants; and,
   a microwave generator for supplying microwave radiation to the matrix core;
   wherein, when the matrix core is supplied with microwave radiation and a pressurized gas stream is introduced into the treatment chamber the matrix core is subjected to microwave radiation and elevated temperatures, the combination of radiation and elevated temperatures destroying organic contaminants within the pressurized gas stream.

2. The process according to claim 1 wherein the treatment chamber further defines an ion exchange material adapted for removing specific constituents from the pressurized gas stream.

3. A process of treating a gas waste stream comprising:
   passing the gas waste stream into a treatment chamber;
   radiating the waste stream in the treatment chamber with microwave energy;
   retaining the waste stream within the treatment chamber until an effective amount of the waste stream gases are destroyed or decomposed, thereby providing a treated off-gas; and,
   venting the treated off-gas.

4. The process according to claim 3 wherein the waste gas treatment process further comprises:
   detecting the off-gas for a known off-gas constituent;
   comparing a concentration value of the off-gas constituent to a pre-set threshold value;
   venting the off-gas when the constituent value is below the threshold value;

re-directing the off-gas constituent through a second treatment chamber when the contaminant value is above a threshold limit; and, continuing to pass the off-gas containing the elevated contaminant level through the treatment chamber until the contaminant level falls below the threshold value.

5. The process according to claim 3 comprising the additional step of subjecting the gas waste stream in the treatment chamber to a temperature of at least about 1000° C.

6. The process according to claim 3 wherein the treatment chamber further defines an ion exchange material adapted for removing specific constituents from the waste gas stream.

7. The process according to claim 3 comprising the additional step of subjecting the gas waste stream in the treatment chamber to a temperature of at least about 1000° C.

* * * * *